US00PP12140P2

(12) United States Plant Patent
Herndon

(10) Patent No.: US PP12,140 P2
(45) Date of Patent: Oct. 9, 2001

(54) CLERODENDRUM PLANT NAMED 'BRANDONII'

(75) Inventor: Mark B. Herndon, Ft. Lauderdale, FL (US)

(73) Assignee: Black Olive East Nursery, Ft. Lauderdale, FL (US)

( * ) Notice: Subject to any disclaimer, the term of this patent is extended or adjusted under 35 U.S.C. 154(b) by 0 days.

(21) Appl. No.: 09/330,005

(22) Filed: Jun. 11, 1999

(51) Int. Cl.[7] ..... A01H 5/00
(52) U.S. Cl. ..... Plt./226

(58) Field of Search ..... Plt./226

*Primary Examiner*—Bruce R. Campell
*Assistant Examiner*—Susan B. McCormick
(74) *Attorney, Agent, or Firm*—Foley & Lardner

(57) ABSTRACT

A Clerodendrum plant named 'Brandonii' characterized by having distinctive variegation on the upper surface of leaves which are dark-green with irregular patchy lighter green becoming cream colored towards the edge. The variegation becomes yellow in full sunlight but remains cream-colored in partial shade. The edges of leaves appear somewhat deformed especially around heavy areas of variegation. The growth rate of 'Brandonii' is approximately 50% slower than the parent selection.

2 Drawing Sheets

BACKGROUND OF THE INVENTION

The present invention comprises a new and distinct cultivar of Clerodendrum known by the cultivar name 'Brandonii'.

The new cultivar was selected by the inventor, Mark B. Herndon, in Ft. Lauderdale, Fla., in 1995. The cultivar was discovered by the inventor as a naturally occurring mutation of *Clerodendrum quadriloculare* commonly known by the name 'Shooting Star'.

Asexual reproduction of the new cultivar by vegetative cuttings was performed by the inventor in a controlled environment in June, 1995, in Ft. Lauerdale, Fla., and has demonstrated that the combination of characteristics as herein disclosed for 'Brandonii' are firmly fixed and retained through successive generations of asexual reproduction.

BRIEF DESCRIPTION OF THE INVENTION

The following traits have been repeatedly observed and are determined to be basic characteristics of 'Brandonii' which in combination distinguish this Clerodendrum as a new and distinct cultivar:

1. distinctive variegation on the upper surface of leaves which are dark-green with irregular patchy lighter green becoming cream colored towards the edge;
2. variegation becomes yellow in full sunlight but remains cream-colored in partial shade;
3. edges of leaves appear somewhat deformed especially around heavy areas of variegation; and
4. growth rate approximately 50% slower than the parent selection.

'Brandonii' has not been observed under all possible environmental conditons. The phenotype of the new cultivar may vary significantly with variations in environment such as temperature, light intensity, and daylength without any change in genotype.

Of the many commercial cultivars known to the present invention, the most similar in comparison to 'Brandonii' is the parent *C. quadriloculare* named 'Shooting Star' (unpatented). 'Brandonii' plants are shorter, bushier, and grow more slowly than 'Shooting Star'. The leaves of 'Brandonii' are flatter and stiffer than the leaves of 'Shooting Star'. The upper surface of the leaves of 'Brandonii' are tri-colored and show more irregular variegation and quilting than the leaves of 'Shooting Star' which are primarily dark-green in color. 'Brandonii' shows similar flower characteristics as 'Shooting Star', but the exterior throat color is slightly paler for flowers of 'Brandonii'.

BRIEF DESCRIPTION OF THE DRAWING

The accompanying photographic illustration shows a typical 'Brandonii' plant following growth under appropriate growing conditions, with colors being as true as possible with illustrations of this type.

FIG. 1 is a top view of a flower of 'Brandonii'.

FIG. 2 is a close-up view of the leaves of 'Brandonii' showing the distinctive variegation.

DETAILED BOTANICAL DESCRIPTION

The following observations, measurements and values describe the new cultivar as grownin Ft. Lauderdale, Fla., in full and partial sun, under conditions which closely approximate those generally used in commerical practice. The age of the observed plant is 5 years old. Color references are made to The Royal Horticultural Society Colour Chart (R.H.S.), except where general colors of ordinary significance are used. The color values were determined in Washington, D.C. by reviewing various color photographs of a typical 'Brandonii' plant.

Origin: Ft. Lauderdale, Fla.

Classification:

*Botanical.*—*Clerodendrum quadriloculare* (Tricolor) 'Brandonii'.

*Commercial.*—Clerodendrum cultivar c.v. 'Brandonii'.

Plant:

*Growth habit.*—Large upright to rounded shrub. New growth emerges green with slight yellow variegation on the edges of the leaves. Older growth becomes heavily variegated around the leaves' edges with purple through the center of the leaf.

*Height.*—Up to 15–20 feet.

*Spreading area.*—Approximately 10 feet.

*Blooming period.*—January to April, in South Florida.

*Cold hardiness.*—Zone 10 tolerance.

Stem:

*Thickness.*—Approximately 4 inches, at the point of plant maturity.

*Color.*—Dark-purple (RHS 79D) becoming green (RHS 137C) then tan (RHS 199D) at maturity.

*Branching.*—Opposite.

*Length of internode.*—Approximately 4–5 inches as plant matures to 3–4 feet.

Leaf:

*Appearance.*—Leaves are undulate with variegation, giving the appearance of deformity.

*Arranngement on stem.*—Opposite.

*Leaves per stem.*—6–12 per foot of stem.

*Shape.*—Lanceolate elliptic.

*Width.*—Up to 8 inches.

*Length.*—Up to 8 inches.

*Thickness.*—Between ¼ and ½ mm.

*Base.*—Acute.

*Apex.*—Acuminate.

*Margin.*—Undulate.

*Venation pattern.*—Pennate.

*Leaf stem.*—Stalked.

*Color.*—Upper Surface: Dark-green (RHS 133A) to irregular light-green (RHS 133C) and cream (RHS 8C). Under Surface: Purple (RHS 59A).

*Petiole.*—¾ inch long.

Umbel:

*Spread.*—2.5–4 inches.

*Height.*—1–1.5 inches.

*Number of flowers per umbel.*—Approximately 65–80.

Flower:

*Orientation at opening.*—Upright.

*Type.*—Multiple in oppositely branched panicle of umbels.

*Shape.*—Salverform with recurved petals.

*Diameter.*—¾ inch.

*Tube length.*—3½ inches.

*Color.*—Bud: Purple (RHS 78B) becoming lavender streaked (RHS 77C) with cream (RHS 11D). Tube of flower: Fuchsia (RHS 68B). Petals: Cream-faced (RHS 11D) upon opening (both surfaces).

*Number.*—Approximately 65 to 85 per umbel.

*Petals.*—Tube Length: 3½ inches. Width: ¾ inch. Texture: Smooth.

*Sepals.*—Length: 3½ inches. Width: ¾ inch. Color: Pale pink.

*Buds.*—Length: 4 inches. Width: 6 inches. Shape: Round.

Reproductive organs:

*Pistil.*—Number: 1. Color: Lavender (RHS 77B). Shape: Bifurcate. Length: ¼ inch.

*Stamens.*—4, brown.

*Anther.*—First yellow (RHS 11B) then dark-green (RHS 133A) then black (RHS 202A).

*Filament.*—Cream (RHS 10D).

*Ovary.*—Round and green.

*Pollen color.*—Clear.

*Flower duration.*—Approximately 1 to 3 days (Cluster opens gradually).

Fragrance: None.

Fruit seed set: No known fruit or seed.

Disease resistance: Resistance to disease/insects of the genus/species has not been observed.

I claim:

1. A new and distinct Clerodendrum plant named 'Brandonii', substantially as illustrated and described herein.

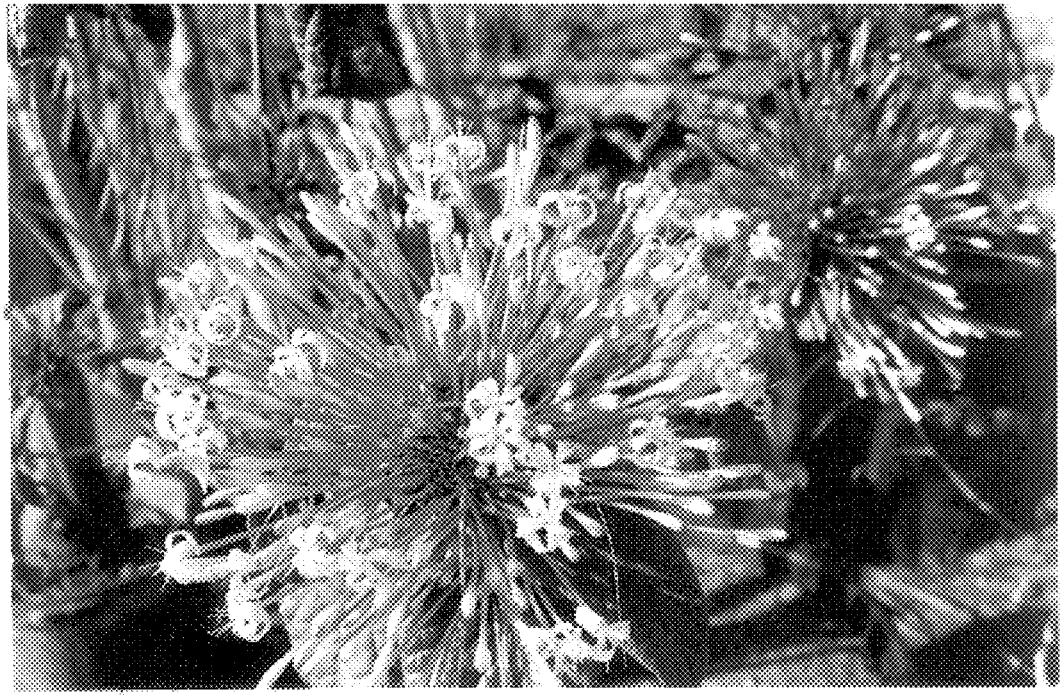

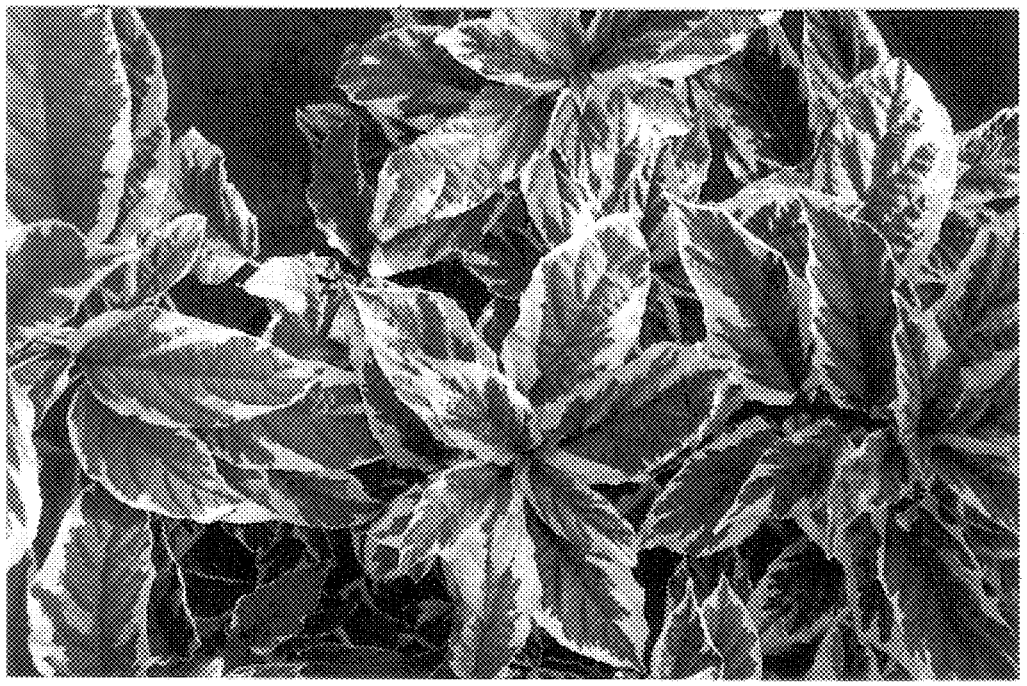

* * * * *